US00PP16196P2

(12) United States Plant Patent
Suzuki

(10) Patent No.: US PP16,196 P2
(45) Date of Patent: Jan. 10, 2006

(54) ***PELARGONIUM* PLANT NAMED 'SURFING LILAC'**

(50) Latin Name: *Pelargonium domesticum*
Varietal Denomination: Surfing Lilac

(75) Inventor: Seiji Suzuki, Chigasaki (JP)

(73) Assignee: Sakata Seed Corporation, Yokohama (JP)

( * ) Notice: Subject to any disclaimer, the term of this patent is extended or adjusted under 35 U.S.C. 154(b) by 106 days.

(21) Appl. No.: 10/964,159

(22) Filed: Oct. 12, 2004

(51) Int. Cl.
*A01H 5/00* (2006.01)

(52) U.S. Cl. ..... Plt./324

(58) Field of Classification Search ..... Plt./324
See application file for complete search history.

*Primary Examiner*—Kent Bell
(74) *Attorney, Agent, or Firm*—Jondle & Associates, P.C.

(57) ABSTRACT

A *Pelargonium* cultivar particularly distinguished by light purple flower color, upright growth habit and early maturation.

1 Drawing Sheet

Genus and species: *Pelargonium domesticum.*
Variety denomination: 'Surfing Lilac'.

BACKGROUND OF THE NEW PLANT

The present invention comprises a new and distinct cultivar of geranium, botanically known as *Pelargonium domesticum,* and hereinafter referred to by the cultivar name 'Surfing Lilac'. It is characterized by having a light purple flower color, upright growth habit and early maturation. The new cultivar originated from an open pollinated population of *Pelargonium* which consisted of one female *Pelargonium* line and approximately 100 male breeding lines in Kanegawa, Japan in 2001. The female parent breeding line is the publicly available *Pelargonium* variety 'Surfing Purple' (Japan PBR #11363, available in Japan). The male parent is an unnamed breeding line of unknown origin.

F1 seed from the hybridization was harvested from the female parent and sown in the greenhouse in 2001. F1 plants were observed and one plant was selected based on its light purple flower color, growth habit, early maturity, flower size, and multiple inflorescences per plant. The plant was then asexually propagated through cuttings in both Kanagawa, Japan and Salinas, Calif. The plant was further evaluated in the greenhouse from 2001 through 2003 to establish the uniformity and stability of its characteristics. The plant has been shown to reproduce true to type in successive generations of asexual propagation.

DESCRIPTION OF PHOTOGRAPHS

This new geranium plant is illustrated by the accompanying photographs which show the overall plant habit and a mature inflorescence of the plant in full color, the colors shown being as true as can be reasonably obtained by conventional photographic procedures.

DESCRIPTION OF THE NEW CULTIVAR

Figure 1:
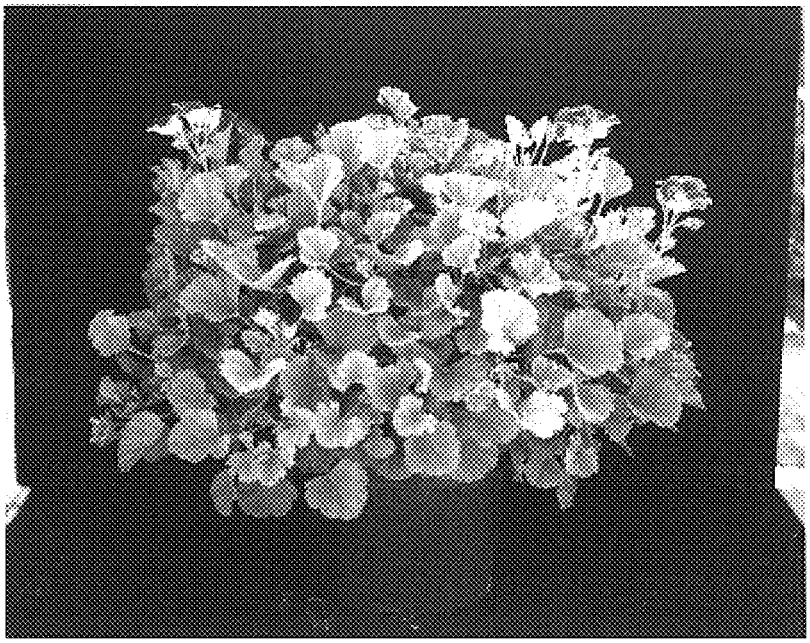
FIG. 1 shows overall plant habit.
Figure 2:
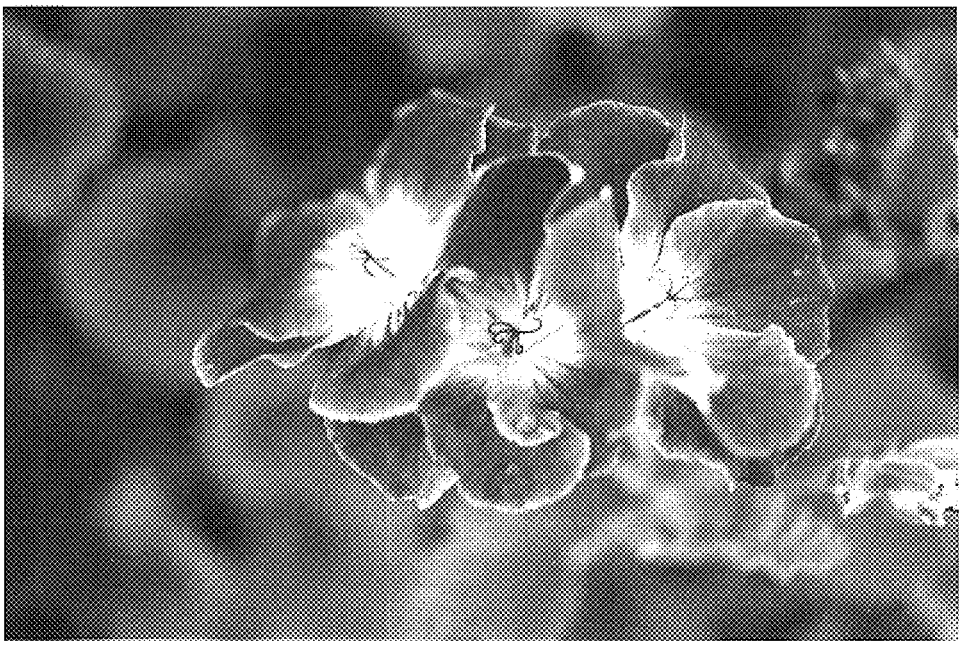
FIG. 2 shows the mature inflorescence.

The following detailed descriptions set forth the distinctive characteristics of 'Surfing Lilac'. The data which define these characteristics were collected from asexual reproductions carried out in Salinas, Calif. The plant history was taken on 20-week-old plants grown under greenhouse conditions. Color references are to The R.H.S. Colour Chart of The Royal Horticultural Society of London (R.H.S.).

DETAILED BOTANICAL DESCRIPTION

Classification:
- *Family.*—Geraniacaea sub.f. Geranioideae.
- *Species.*—*Pelargonium domesticum.*
- *Common name.*—*Pelargonium* (Geranium).

Plant:
- *Habit.*—Upright and compact.
- *Height.*—35 cm as measured from soil level to top of plant.
- *Spread.*—70 cm.
- *Life cycle.*—Perennial.
- *Form.*—Highly branching.
- *Time to produce a rooted cutting.*—6–8 weeks.
- *Time to bloom from propagation.*—16–20 weeks.
- *Flowering requirements.*—Will flower as long as day length is greater than 12 hours and temperature is above 9° C. for at least 10 hours per day for a minimum of 4 weeks.

Propagation: The terminal 1.0 to 1.5 inches of an actively growing stem was excised. The vegetative cuttings were propagated in approximately 4–6 weeks. The base of each cutting was dipped for 1 to 2 seconds in a 1:9 solution of Dip'N Grow root inducing solution immediately prior to being placed into cell trays. The cuttings were placed into plastic cell trays having 98 cells and containing a moistened peat moss-based growing medium. The cuttings were misted with water from overhead for 10 seconds every 30 minutes for 3 days. After 3 days, misting was decreased over a period of 2 weeks, upon which time sufficient roots were formed. Rooted cuttings were transplanted and grown in 20 cm diameter plastic pots in a greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow-release fertilizer containing 20% nitrogen, 10% phosphorous and 18% potassium. The typical average air temperature was 24° C.

Stems:

*Stem color.*—RHS 143A (green).

*Anthocyanin color.*—RHS 64B (red-purple); present at upper tip of pedicel.

*Pubescence.*—Heavy.

*Pubescence color.*—RHS N155A (white).

*Stem form.*—Round; woody at soil line.

*Stem length.*—About 1.5 cm. from soil line to first node.

*Stem diameter.*—1.0–1.2 cm between $1^{st}$ and $2^{nd}$ nodes; 5 mm near peduncles.

*Internode length.*—2.0–6.0 cm.

Leaves:

*Leaf arrangement.*—Opposite.

*Leaf shape.*—Curled, Spatulate.

*Leaf tip.*—Mucronate.

*Leaf base.*—Acuminate.

*Leaf margin.*—Serrate.

*Leaf surface.*—Dull.

*Leaf length.*—4.5–4.8 cm.

*Leaf width.*—4.5–5.5 cm.

*Leaf color.*—Upper surface: RHS 137B (green). Lower surface: RHS 138B (green).

*Leaf fragrance.*—None.

*Leaf surface pubescence.*—Slight.

*Leaf surface pubescence color.*—RHS N155A (white).

*Petiole length.*—2.0–2.8 cm.

*Petiole color.*—RHS 143A (green).

*Venation.*—Pinnate.

*Venation color.*—RHS 138B (green).

Inflorescence:

*Flowering habit.*—Umbels.

*Lastingness of individual blooms.*—About 14 days.

*Umbel diameter.*—10.0 cm.

*Umbel depth.*—4.5–5 cm.

*Flower buds.*—Cluster shape: 5 buds arranged radially on peduncle with a $6^{th}$ bud rising vertically from the center. Individual bud shape: Deltoid, pointed at tip; Margin: entire. Cluster size: Depth: 1.0–1.4 cm; Diameter: 0.4–0.5 cm. Color: RHS 143B (green).

*Corolla diameter.*—4.5 cm.

*Corolla depth.*—2.5 cm.

*Ovary.*—Superior.

*Petal pubescence.*—Glabrous.

*Petals.*—Length: 3.0–3.2 cm. Width: 2.3–2.5 cm. Number: 5. Shape: Spatulate. Apex: Mucronate. Base: Decurrent. Margin: Crenate/undulating. Color: Lobes: Upper: RHS N74C (red-purple) with three large RHS N74A (red-purple) veins. Lower: N155A (white). Corolla tube: Inner: RHS N155A (white) with RHS N77A (red-purple) specks. Outer: RHS N155A (white) with RHS N74A (red-purple) streaking and veins.

*Fragrance.*—Absent.

*Sepals.*—Number per flower: 5. Shape: Lanceolate. Apex: Acute. Margin: Entire. Color: RHS 143B (green) (both surfaces). Size: Length: 1.4–1.6 cm; Width: 0.4–0.5 cm.

*Pedicel.*—Length: 2.0 cm. Diameter: 2 mm. Color: Base: RHS 141B (green); Tip: RHS 64B (red-purple).

*Peduncle.*—Length: 4.0–5.0 cm. Diameter: 4–5 mm. Color: RHS 143A (green).

Reproductive organs:

*Stamens.*—Anther length: 0.3–0.4 cm. Filament length: 1.0–1.3 cm. Filament color: RHS N155A (white). Pollen number: Too numerous to count. Pollen color: RHS 16C (yellow-orange).

*Pistils.*—Number: 1 per corolla. Stigma color: RHS 71A (red-purple). Style length: 1.3 cm. Style color: RHS 61C (red-purple). Ovary arrangement: Superior.

Disease and Insect Resistance

No unique or distinguishing resistance or susceptibility observed.

Comparison with Known Cultivars

*Pelargonium* 'Surfing Lilac' is a unique variety of *Pelargonium* due to its light purple flower color, upright growth habit and early maturity. 'Surfing Lilac' is most similar to the *Pelargonium* variety 'Surfing Purple' (Japan PBR #11363), which was the female parent, however, there are differences as noted in the table below. A comparison with the male parent is not possible because it is unknown which of the 100 male lines served as the male parent.

TABLE 1

| Characteristic | 'Surfing Lilac' | 'Surfing Purple' |
|---|---|---|
| Flower color | RHS N74C (red-purple) with RHS N74A (red-purple) veins | RHS N74A (red-purple) with RHS N72A (red-purple) veins |
| Petal length | 3.0–3.2 cm | 4.0–4.5 cm |
| Time to Bloom | 16–20 weeks from rooted cutting | 18–22 weeks from rooted cutting |

I claim:

1. A new and distinct cultivar of *Pelargonium* plant as shown and described herein.

* * * * *